(12) United States Patent
Callaghan et al.

(10) Patent No.: US 10,918,515 B2
(45) Date of Patent: Feb. 16, 2021

(54) VAGINAL RING APPLICATOR

(71) Applicant: Merck Sharp & Dohme B.V., Haarlem (NL)

(72) Inventors: Owen Callaghan, Den Bosch (NL);
Cornelis P. M. Govers, Bergham (NL);
Joris M. Swaak, Deventer (NL);
Marco A. Voogsgerd, Deventer (NL);
Mario A. A. de Zeeuw, Deventer (NL);
Jesper Laursen, Alslev (DK); Klaas Sipkens, Alslev (DK)

(73) Assignee: Merck Sharp & Dohme B.V., Haarlem (NL)

( * ) Notice: Subject to any disclaimer, the term of this patent is extended or adjusted under 35 U.S.C. 154(b) by 460 days.

(21) Appl. No.: 15/559,099

(22) PCT Filed: Mar. 30, 2016

(86) PCT No.: PCT/EP2016/056925
§ 371 (c)(1),
(2) Date: Sep. 18, 2017

(87) PCT Pub. No.: WO2016/156403
PCT Pub. Date: Oct. 6, 2016

(65) Prior Publication Data
US 2018/0243125 A1    Aug. 30, 2018

Related U.S. Application Data

(60) Provisional application No. 62/275,324, filed on Jan. 6, 2016, provisional application No. 62/140,580, filed on Mar. 31, 2015.

(51) Int. Cl.
*A61F 6/12*     (2006.01)
*A61K 9/00*    (2006.01)
(Continued)

(52) U.S. Cl.
CPC .................. *A61F 6/12* (2013.01); *A61F 6/08* (2013.01); *A61F 13/26* (2013.01); *A61F 13/266* (2013.01);
(Continued)

(58) Field of Classification Search
CPC ........ A61F 13/26; A61F 13/266; A61F 13/28; A61F 6/08; A61F 6/12; A61F 2002/0072;
(Continued)

(56) References Cited

U.S. PATENT DOCUMENTS 2,008,380 A    7/1935    Bachmann
2,830,582 A    4/1958    Ljung
(Continued)

FOREIGN PATENT DOCUMENTS

WO    WO1997002015 A1    1/1997
WO         1999038468 A1    8/1999
(Continued)

OTHER PUBLICATIONS

Kottawar, Shrinivas, S. et al, Synthesis and Antimicrobial Evaluation of Some Heterocyclic Sulfonamide Derivatives, Heteroletters, 2013, p. 31-36, vol. 3, No. 1.

*Primary Examiner* — Ophelia A Hawthorne
*Assistant Examiner* — Caitlin A Carreiro
(74) *Attorney, Agent, or Firm* — Janet E. Fair; Catherine D. Fitch

(57) ABSTRACT

A vaginal ring applicator having a polymeric barrel and at least one friction reducing agent, wherein the barrel is a flattened cylinder having two slightly curved and opposing sides connected by two arcs, wherein the barrel extends between an insertion end and a plunger end; and a plunger extending between distal and proximal ends, wherein the
(Continued)

distal end of the plunger engages the plunger end of the barrel and wherein the plunger fits telescopically within the barrel.

19 Claims, 7 Drawing Sheets

(51) Int. Cl.
| | |
|---|---|
| *A61F 13/28* | (2006.01) |
| *A61F 13/26* | (2006.01) |
| *A61F 6/08* | (2006.01) |
| *A61K 31/565* | (2006.01) |
| *A61L 31/14* | (2006.01) |
| *B29C 45/26* | (2006.01) |
| *B29K 23/00* | (2006.01) |
| *B29L 31/00* | (2006.01) |

(52) U.S. Cl.
  CPC ............ *A61F 13/28* (2013.01); *A61K 9/0036* (2013.01); *A61K 31/565* (2013.01); *A61L 31/14* (2013.01); *B29C 45/261* (2013.01); *A61L 2400/10* (2013.01); *B29K 2023/12* (2013.01); *B29L 2031/753* (2013.01)

(58) Field of Classification Search
  CPC .. A61F 2/0036; A61F 6/00; A61F 6/06; A61F 6/14; A61F 6/18; A61F 6/20; A61K 31/565; A61K 9/0036; A61K 9/0024; A61K 9/0034; A61K 9/0039; A61L 2400/10; A61L 31/14; B29C 45/261; B29K 2023/12; B29L 2031/753; A61B 17/42
  USPC ........ 128/838, 840, 831, 834, 830; 424/423, 424/430, 432, 448, 431; 604/355; 600/30, 37
  See application file for complete search history.

(56) References Cited

U.S. PATENT DOCUMENTS

| | | | | |
|---|---|---|---|---|
| 3,492,990 | A | | 2/1970 | Clarke |
| 4,012,496 | A | | 3/1977 | Schopflin et al. |
| 4,356,817 | A | * | 11/1982 | McKibben ................ A61F 6/12 128/838 |
| 4,398,532 | A | | 8/1983 | Sweeney, III |
| 4,595,000 | A | | 6/1986 | Hamou |
| 4,708,134 | A | | 11/1987 | Wildemeersch |
| 4,766,194 | A | * | 8/1988 | Robertson .......... A63B 37/0001 528/28 |
| 5,207,232 | A | | 5/1993 | Shihata |
| 5,547,701 | A | * | 8/1996 | Nielsen .................... A61F 13/28 427/2.3 |
| 5,558,631 | A | * | 9/1996 | Campion ................ A61F 13/26 604/13 |
| 5,601,530 | A | | 2/1997 | Nielsen .................... A61F 13/28 604/11 |
| 5,795,320 | A | * | 8/1998 | Nielsen ............... A61M 31/007 604/11 |
| 5,800,377 | A | * | 9/1998 | Campion ................ A61F 13/26 604/13 |
| 5,919,474 | A | | 7/1999 | Place et al. |
| 5,984,888 | A | * | 11/1999 | Nielsen .................... A61F 13/26 604/12 |
| D442,688 | S | | 5/2001 | DeWeerd |
| 8,211,085 | B2 | | 7/2012 | Dovonec |
| 8,613,718 | B2 | | 12/2013 | Karapasha et al. |
| 8,756,791 | B2 | | 6/2014 | Jarmon et al. |
| D726,313 | S | | 4/2015 | Govers et al. |
| 2004/0078013 | A1 | | 4/2004 | Zunker et al. |
| 2004/0249352 | A1 | * | 12/2004 | Swick ..................... A61F 13/26 604/279 |
| 2006/0083778 | A1 | | 4/2006 | Allison et al. |
| 2006/0183724 | A1 | * | 8/2006 | Diliberti ................. A61P 15/12 514/170 |
| 2007/0077269 | A1 | | 4/2007 | Woodward |
| 2007/0219515 | A1 | * | 9/2007 | Marsh .................... A61K 8/342 604/359 |
| 2007/0235035 | A1 | | 10/2007 | Petsch et al. |
| 2008/0009663 | A1 | * | 1/2008 | Bartning ................ A61F 13/26 600/30 |
| 2009/0266367 | A1 | * | 10/2009 | Ziv .......................... A61F 2/005 128/834 |
| 2009/0311305 | A1 | | 12/2009 | Abbott et al. |
| 2012/0220919 | A1 | * | 8/2012 | Paulsen .................. A61L 15/48 604/12 |
| 2013/0217960 | A1 | * | 8/2013 | Arora ..................... A61F 13/26 600/37 |

FOREIGN PATENT DOCUMENTS

| | | | |
|---|---|---|---|
| WO | 2007001888 A2 | 1/2007 | |
| WO | WO2008019093 A2 | 2/2008 | |
| WO | WO-2008102315 A1 * | 8/2008 | ............ A61F 13/28 |
| WO | WO2008102315 A1 | 8/2008 | |
| WO | WO2012065073 A2 | 5/2012 | |
| WO | WO-2014081629 A1 * | 5/2014 | .......... H01B 7/1805 |
| WO | WO2016156403 A1 | 10/2016 | |

\* cited by examiner

VAGINAL RING APPLICATOR

CROSS-REFERENCE TO RELATED APPLICATIONS

This application is a U.S. National Phase application under 35 U.S.C. § 371 of PCT Application No. PCT/EP2016/056925, filed Mar. 30, 2016, which published as WO2016/156403 A1 on Oct. 6, 2016, and claims priority under 35 U.S.C. § 365(b) from United States provisional patent application Nos. 62/275,324, filed Jan. 6, 2016 and 62/140,580, filed Mar. 13, 2015.

FIELD OF THE INVENTION

The present invention relates to an applicator for delivering intravaginal devices into the body. Specifically, the invention is directed to a vaginal ring applicator having a barrel and a plunger as well as methods of manufacturing such a vaginal ring applicator.

BACKGROUND

Intravaginal devices are used by women for a variety of reasons. One reason women use intravaginal devices is for birth control; such devices include vaginal rings and intrauterine systems (IUS). Vaginal rings are primarily inserted by digital insertion which may not be the preference of every user. Vaginal ring applicators are disclosed in the art, for example, D442,688.

The most common intravaginal devices are tampons which can be inserted into the body by either digital insertion or are optionally inserted by the use of an applicator. The prior art includes multiple examples of tampon applicators, see U.S. Pat. No. 8,756,791 and U.S. Pat. No. 8,613,718. One may assume that it would be easy to use a tampon applicator to insert a vaginal ring; however, this is not the case. Insertion of a vaginal ring requires, apart from being of suitable size, an applicator with a specific shape unlike the traditional cylindrical shape of most tampon applicators. Additionally, vaginal ring applicators must be composed of specific materials to insure that the ring does not experience friction as the vaginal ring is being inserted in and expelled from the applicator barrel. Such friction can cause the vaginal ring to become distorted and prevent the vaginal ring from being inserted in the body properly.

SUMMARY

The present invention provides a vaginal ring applicator that enables a vaginal ring to be inserted properly and safely. Described herein are vaginal ring applicators comprising a barrel comprising a polymer and at least one friction reducing agent, wherein the barrel is a flattened cylinder having two slightly curved and opposing sides connected by two arcs, wherein the barrel extends between an insertion end and a plunger end; and a plunger comprising a polymer and at least one friction reducing agent and extending between distal and proximal ends, wherein the distal end of the plunger engages the plunger end of the barrel and wherein the plunger fits telescopically within the barrel.

In certain embodiments, the vaginal ring applicators described herein comprise a barrel, wherein the width of the barrel as measured between the two arcs is between 14-15 mm wide. In certain embodiments, the vaginal ring applicators described herein comprise a barrel, wherein the width of the barrel as measured between the two arcs is about 14.3 mm wide.

In certain embodiments, the vaginal ring applicators described herein comprise a barrel, wherein the height of the barrel as measured between the two slightly curved and opposing sides is between 7-8 mm in height. In certain embodiments, the vaginal ring applicators described herein comprise a barrel, wherein the height of the barrel as measured between the two slightly curved and opposing sides is about 7.5 mm in height.

In certain embodiments, the vaginal ring applicators described herein comprise a plunger, wherein the proximal end of the plunger further comprises a concave shape.

In certain embodiments, the vaginal ring applicators described herein comprise a barrel, wherein the barrel comprises a polymer and the polymer is polypropylene. In certain embodiments, the vaginal ring applicators described herein comprise a barrel, wherein the barrel comprises at least one friction reducing agent. In certain embodiments, the vaginal ring applicators described herein comprise a barrel, wherein the barrel comprises at least one friction reducing agent and the at least one friction reducing agent is polydimethylsiloxane. In certain embodiments, the vaginal ring applicators described herein comprise a barrel, wherein the barrel comprises at least one friction reducing agent and the at least one friction reducing agent is pyrogenic silica.

In certain embodiments, the vaginal ring applicators described herein are co-packaged with a vaginal ring. In certain embodiments, the co-packaged vaginal ring comprises etonogestrel. In certain embodiments, the co-packaged vaginal ring comprises etonogestrel and 17 beta estradiol. In certain embodiments, the co-packaged vaginal ring comprises etonogestrel and ethinyl estradiol.

Also described herein, is a use of a vaginal ring comprising etonogestrel with the vaginal ring applicators described herein.

Also described herein, is a use of a vaginal ring comprising etonogestrel and ethinyl estradiol with the vaginal ring applicators described herein.

Also described herein is a use of a vaginal ring comprising etonogestrel and 17 beta estradiol with the vaginal ring applicators described herein.

Also described herein are uses of vaginal rings comprising ethylene vinylacetate with the vaginal ring applicators described herein.

Also described herein are kits comprising: a vaginal ring applicator comprising a barrel comprising a polymer and at least one friction reducing agent, wherein the barrel is a flattened cylinder having two slightly curved and opposing sides connected by two arcs, wherein the barrel extends between an insertion end and a plunger end; a plunger extending between distal and proximal ends, wherein the distal end of the plunger engages the plunger end of the barrel and wherein the plunger fits telescopically within the barrel, wherein the outer surface is polished; and a vaginal ring comprising etonogestrel and ethinyl estradiol.

Also described herein are kits comprising: a vaginal ring applicator comprising a barrel comprising a polymer and at least one friction reducing agent, wherein the barrel is a flattened cylinder having two slightly curved and opposing sides connected by two arcs, wherein the barrel extends between an insertion end and a plunger end; a plunger extending between distal and proximal ends, wherein the distal end of the plunger engages the plunger end of the barrel and wherein the plunger fits telescopically within the barrel, wherein the outer surface is polished; and a vaginal ring comprising etonogestrel and 17 beta estradiol.

BRIEF DESCRIPTION OF THE FIGURES

The foregoing and other features and advantages of the invention will be apparent from the following, more particular description of a preferred embodiment of the invention, as illustrated in the accompanying drawings wherein like reference numbers generally indicate identical, functionally similar, and/or structurally similar elements.

DESCRIPTION

For the purpose of clarity, orientation references are hereby established for the description of this invention. The term "proximal" refers to the plunger end of the assembled vaginal ring applicator comprising the barrel and the plunger. The term "distal" refers to the insertion end of the assembled vaginal ring applicator comprising the barrel and the plunger i.e. the end from which the ring is expelled from the assembled vaginal ring applicator.

Figure 1:
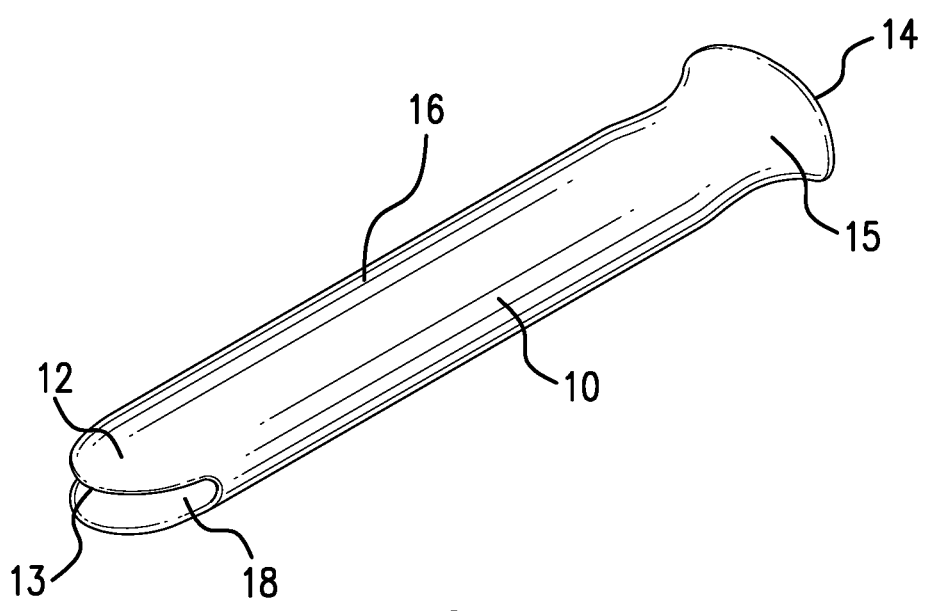
FIG. 1 is a perspective view of an embodiment of the barrel of the vaginal ring applicator described herein.

In the figures, where like reference numerals designate like elements throughout the drawings. FIG. 1 is a perspective view of an embodiment of the barrel of the vaginal ring applicator described herein. FIG. 1 shows an embodiment of the barrel 10 of the vaginal ring applicator described herein. Barrel 10 is a hollow flattened cylinder. The barrel 10 has an inserter end 12 comprising a barrel opening 13 and a plunger end 14 comprising a finger grip 15. The barrel 10 also has an outer surface 16 and an inner surface 18.

The inner surface 18 of the barrel 10 must possess such physical properties such that the intrinsic surface friction between the inner surface 18 of the barrel 10 and the vaginal ring must be low so that the vaginal ring can be easily inserted by the user and the vaginal ring does not become distorted or stuck in the applicator. Most vaginal rings are made of a polymer, such as polyethylene vinyl acetate copolymer, polyurethane or silicone. Such materials when expelled from a vaginal ring applicator made of only polymers can experience high surface friction between the vaginal ring and the inner surface of the vaginal ring applicator.

Therefore, the barrel of the vaginal ring applicator described herein is made of a polymer and at least one friction reducing agent. In certain embodiments, the friction reducing agent is distributed throughout the barrel polymer. In other embodiment, the friction reducing agent is localized on the inner surface of the barrel.

Suitable polymers include, but are not limited to, polypropylene, polyethylene, low density polyethylene, medium density polyethylene, high density polyethylene, linear low density polyethylene, near low density polyethylene, polyethylene terephthalate (PET), nylon, polystyrene, polyvinyl chloride, polymethyl methacrylate, polyolefin elastomer, copolymers of alfa-olefines, and combinations thereof. In one embodiment, the barrel is made of polypropylene.

Suitable friction reducing agents include, but are not limited to, erucamide, demethicone, oleamide and fatty acid amides, polydimethylsiloxane, pyrogenic silica or combinations thereof. In one embodiment, the barrel contains polydimethylsiloxane. In another embodiment, the barrel contains pyrogenic silica. In yet another embodiment, the barrel contains a mixture of polydimethylsiloxane and pyrogenic silica.

The barrel can also comprise a dye in order to impart a particular color to the barrel.

Figure 2:
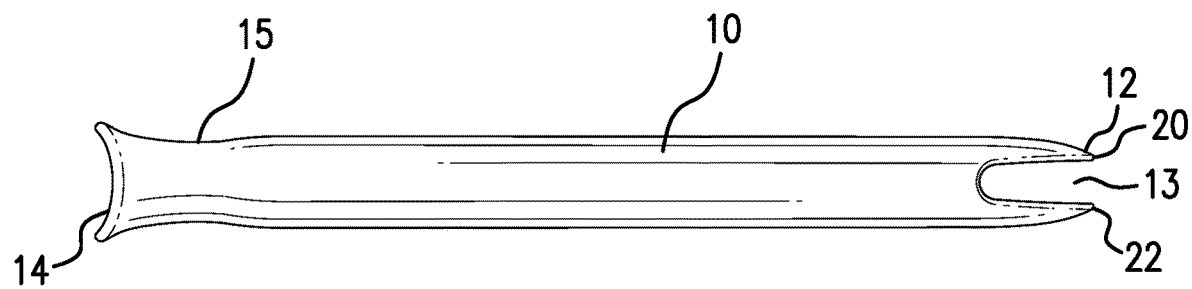
FIG. 2 is a side perspective view of an embodiment of the barrel of the vaginal ring applicator described herein.

FIG. 2 is a side view of an embodiment of the barrel of the vaginal ring applicator described herein. FIG. 2 shows an embodiment of the barrel 10 of the vaginal ring applicator described herein. Barrel 10 is a hollow flattened cylinder. The flattened cylinder shape keeps a vaginal ring in one plane while being inserted into the vaginal ring applicator or expelled from the vaginal ring applicator. If friction between the barrel and the ring is high, the ring will bend and the ring will not be able to be expelled from the barrel of the applicator. As shown in FIG. 2, the barrel 10 has an inserter end 12 and a plunger end 14. Inserter end 12 comprises a barrel opening 13 that is surrounded by a set of two convex end portions, a top convex end portion 20 and a bottom convex end portion 22. It is through the barrel opening 13 of the inserter end 12 that a vaginal ring is loaded or inserted into the vaginal ring applicator. Also shown in FIG. 2, is a plunger end 14 comprising a flared or tulip design that can serve as a finger grip 15 so that the user can comfortably grip the barrel 10.

Figure 3:
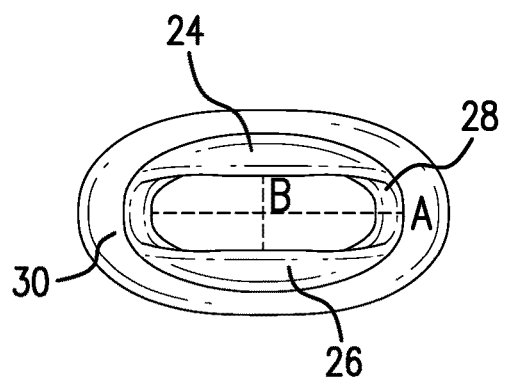
FIG. 3 is a distal frontal view of an embodiment of the barrel of the vaginal ring applicator described herein.

FIG. 3 is a distal frontal view, of an embodiment of the barrel of the vaginal ring applicator described herein. Specifically, FIG. 3 shows the flattened cylinder shape of the barrel has two slightly curved, opposite facing i.e. opposing sides, a top side 24 and a bottom side 26 connected by two arcs, a right arc 28 and a left arc 30.

In certain embodiments of the vaginal ring applicator described herein, the width of the barrel measured along line A as shown in FIG. 3 can be between about 10-20 mm. In other embodiments of the vaginal ring applicator described herein, the width of the barrel of the barrel can be between about 11-19 mm wide. In other embodiments of the vaginal ring applicator described herein, the width of the barrel can be between about 12-18 mm wide. In other embodiments of the vaginal ring applicator described herein, the width of the barrel can be between about 12-17 mm wide. In other embodiments of the vaginal ring applicator described herein, the width of the barrel can be between about 12-16 mm wide. In other embodiments of the vaginal ring applicator described herein, the width of the barrel can be between about 12-15 mm wide. In other embodiments of the vaginal ring applicator described herein, the width of the barrel can be between about 13-15 mm wide. In other embodiments of the vaginal ring applicator described herein, the width of the barrel can be between about 14-15 mm wide.

In certain embodiments of the vaginal ring applicator described herein, the width of the barrel can be about 13.0 mm, 13.1 mm, 13.2 mm, 13.3 mm, 13.4 mm, 13.5 mm, 13.6 mm, 13.7 mm, 13.8 mm, 13.9 mm, 14.0 mm, 14.1 mm, 14.2 mm, 14.3 mm, 14.4 mm, 14.5 mm, 14.6 mm, 14.7 mm, 14.8 mm, 14.9 mm, 15.0 mm, 15.1 mm, 15.2 mm, 15.3 mm, 15.4 mm, 15.5 mm, 15.6 mm, 15.7 mm, 15.8 mm, 15.9 mm or 16.0 mm wide. In some embodiments of the vaginal ring applicator described herein, the width of the barrel is 14.3 mm wide.

In certain embodiments of the vaginal ring applicator described herein, the height of the barrel measured along line B as shown in FIG. 3 can be between about 3-10 mm in height. In other embodiments of the vaginal ring applicator described herein, the height of the barrel of the barrel can be between about 3.5-9.5 mm in height. In other embodiments of the vaginal ring applicator described herein, the height of the barrel can be between about 4-9 mm in height. In other embodiments of the vaginal ring applicator described herein, the height of the barrel can be between about 4.5-8.5 mm in height. In other embodiments of the vaginal ring applicator described herein, the height of the barrel can be between about 5-8 mm in height. In other embodiments of the vaginal ring applicator described herein, the height of the barrel can be between about 5.5-7.5 mm in height. In other embodiments of the vaginal ring applicator described herein, the height of the barrel can be between about 6-7.5 mm in height. In other embodiments of the vaginal ring applicator described herein, the height of the barrel can be between about 6.5-7.5 mm in height.

In certain embodiments of the vaginal ring applicator described herein, the height of the barrel can be about 6.0 mm, 6.1 mm, 6.2 mm, 6.3 mm, 6.4 mm, 6.5 mm, 6.6 mm, 6.7 mm, 6.8 mm, 6.9 mm, 7.0 mm, 7.1 mm, 7.2 mm, 7.3 mm, 7.4 mm, 7.5 mm, 7.6 mm, 7.7 mm, 7.8 mm, 7.9 mm, 8.0 mm, 8.1 mm, 8.2 mm, 8.3 mm, 8.4 mm, 8.5 mm, 8.6 mm, 8.7 mm, 8.8 mm, 8.9 mm or 9.0 mm wide. In some embodiments of the vaginal ring applicator described herein, the width of the barrel is 7.5 mm in height.

Figure 4:
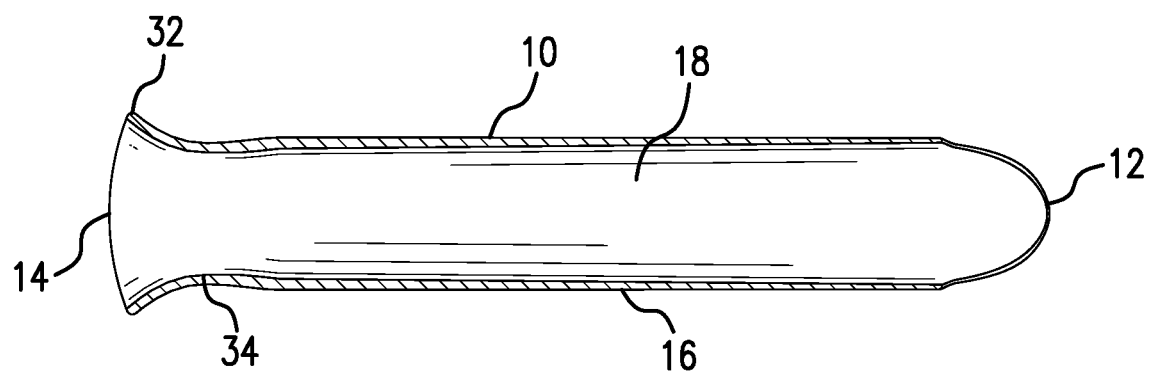
FIG. 4 is a cross-section view of an embodiment of the barrel of the vaginal ring applicator described herein.

FIG. 4 is a cross-section view of an embodiment of the barrel of the vaginal ring applicator described herein. FIG. 4 shows an embodiment of the barrel 10 of the vaginal ring applicator described herein. The barrel 10 has an inserter end 12 and a plunger end 14. The barrel 10 also has an outer surface 16 and an inner surface 18. As shown in the embodiment of barrel 10 in FIG. 4, the plunger end 14 of barrel 10 has a fluted or tulip design comprising a narrow portion 34 and a wider portion 32. The narrow portion 34 of the fluted or tulip design provides a stopping point for the plunger so that the plunger and barrel cannot be easily separated.

Figure 5:
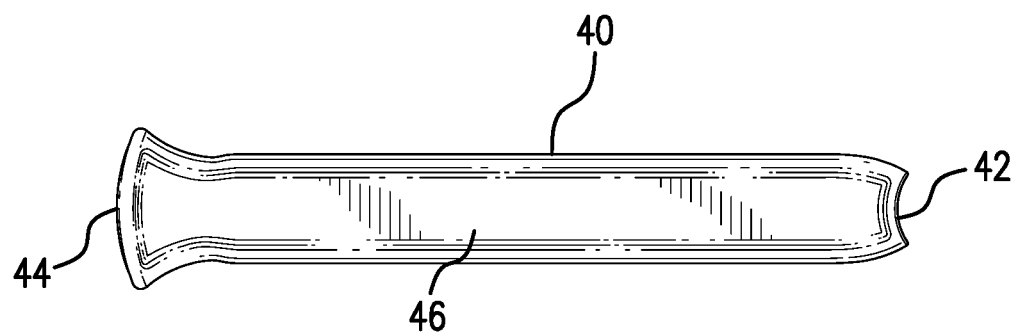
FIG. 5 is a top perspective view of an embodiment of the plunger of the vaginal ring applicator described herein.

FIG. 5 is a top perspective view of an embodiment of the plunger of the vaginal ring applicator described herein. The plunger 40 extends between a distal end 42 and a proximal end 44, and has an outer surface 46. The distal end 42 of the plunger telescopically engages the plunger end of the barrel and further the distal end 42 engages the vaginal ring when the vaginal ring is loaded into the vaginal ring applicator. The plunger 40 is capable of fitting telescopically within the barrel. The distal end 42 of plunger 40 has a concave shape. The shape of the distal end 42 of the plunger 40 should be complementary to the convex shape of a vaginal ring inserted into the vaginal ring applicator. In certain embodiments, the radius of the distal end of the plunger is comparable to the radius of a vaginal ring when inserted into the barrel, facilitating a force transmission from plunger to vaginal ring without generating additional force perpendicular on the inner surface of the barrel (normal force) that would increase friction between ring and barrel.

The plunger of the vaginal ring applicator described herein can be made of the same or a different material as the barrel. In certain embodiments, the plunger is made of a polymer and a friction reducing agent. In certain embodiments, the plunger described herein is made of a polymer.

Suitable polymers include, but are not limited to, polypropylene, polyethylene, low density polyethylene, medium density polyethylene, high density polyethylene, linear low density polyethylene, near low density polyethylene, polyethylene terephthalate (PET), nylon, polystyrene, polyvinyl chloride, polymethyl methacrylate, polyolefin elastomer, copolymers of alfa-olefines, and combinations thereof. In one embodiment, the vaginal ring applicator is made of polypropylene.

Suitable friction reducing agents include, but are not limited to, erucamide, demethicone, oleamide and fatty acid amides, polydimethylsiloxane, pyrogenic silica or combinations thereof. In one embodiment, the barrel contains polydimethylsiloxane. In another embodiment, the barrel contains pyrogenic silica. In yet another embodiment, the barrel contains a mixture of polydimethylsiloxane and pyrogenic silica.

The plunger can further comprise a dye in order to impart a particular color to the barrel.

Making the plunger of the same materials as the barrel of the vaginal ring applicator described herein is, for one reason, ease of manufacturing. In certain embodiments, the plunger can be made of polymer alone, without a friction reduction agent.

In certain embodiments the plunger is solid. In other embodiments, the plunger can be hollow. In certain embodiments, the plunger can be a single piece. In other embodiments, the plunger can be made of several pieces secured together i.e. two halves.

Figure 6:
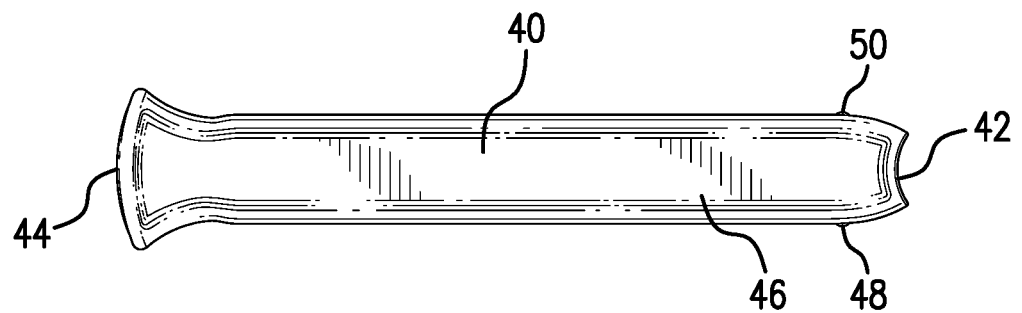
FIG. 6 is a top perspective view of an embodiment of the plunger of the vaginal ring applicator described herein.

FIG. 6 is a top perspective view of another embodiment of the plunger of the vaginal ring applicator described herein. The plunger 40 extends between a distal end 42 and a proximal end 44, and has an outer surface 46 wherein the distal end 42 of the plunger telescopically engages the plunger end of the barrel and further the distal end 42 engages the vaginal ring when the vaginal ring is loaded into the vaginal ring applicator. As shown in the embodiment of FIG. 6, plunger 40 has protrusions 48 and 50. Protrusions 48 and 50 engage with the narrow portion of the fluted or tulip design of the plunger end of the barrel so that the barrel and plunger cannot be easily separated.

Figure 7:
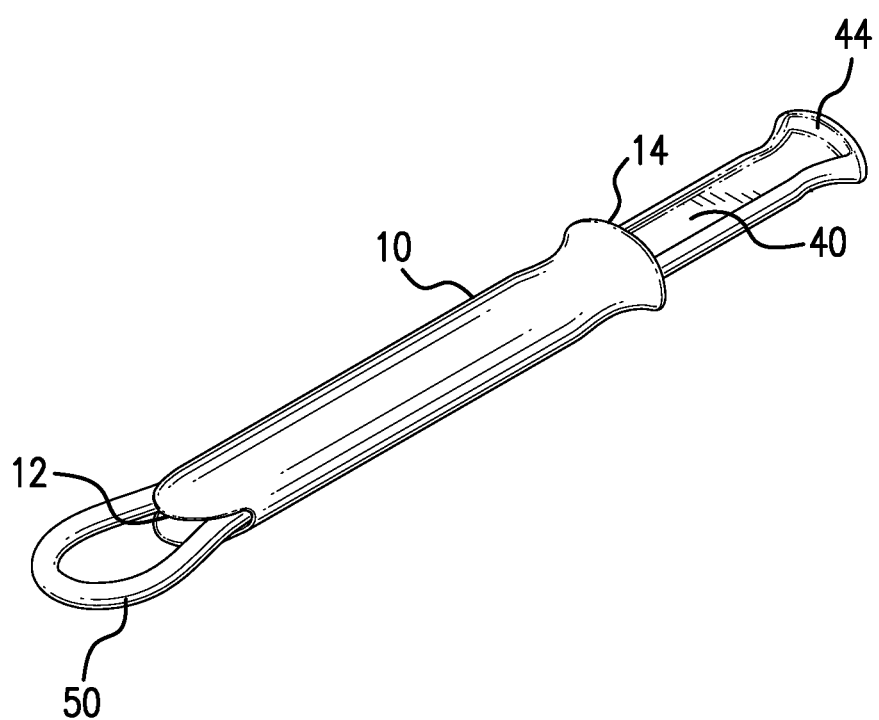
FIG. 7 is a top perspective view of the combined barrel, plunger and vaginal ring.

FIG. 7 is a top perspective view of the combined barrel, plunger and vaginal ring. FIG. 7 shows an embodiment of the barrel 10 of the vaginal ring applicator described herein. The barrel 10 has an inserter end 12 and a plunger end 14. FIG. 7 also shows plunger 40. The plunger 40 is capable of fitting telescopically within the barrel 10. As shown in FIG. 7, plunger 40 is partially inserted into the barrel 10 such that the distal end of the plunger 40 is no longer in view and only the proximal end 44 is exposed. Also shown in FIG. 7 is vaginal ring 50 which is partially loaded into barrel 10.

Figure 8:
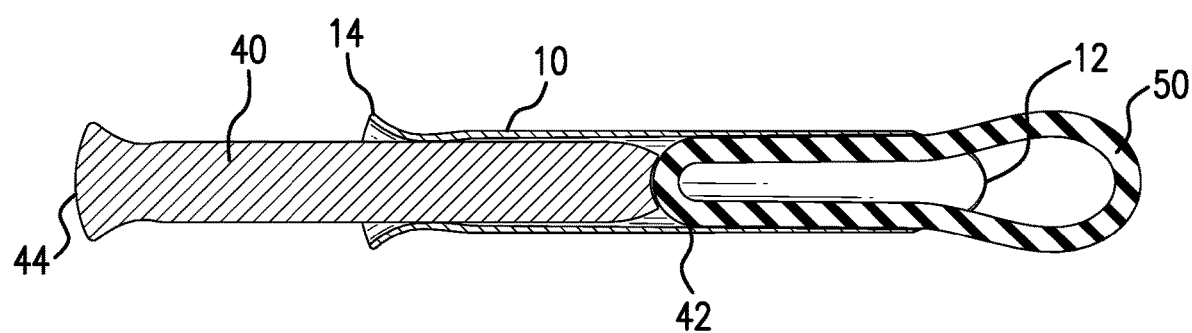
FIG. 8 is a cross section view of the combined barrel, plunger and vaginal ring.

FIG. 8 is a cross section view of the combined barrel, plunger and vaginal ring of FIG. 7. FIG. 8 shows an embodiment of the barrel 10 of the vaginal ring applicator described herein. The barrel 10 has an inserter end 12 and a plunger end 14. FIG. 8 also shows plunger 40. The plunger 40 is capable of fitting telescopically within the barrel 10. As shown in FIG. 8, plunger 40 is partially inserted into the barrel 10 such that the distal end of the plunger 40 is no longer in view and only the proximal end 44 is exposed. Also shown in FIG. 8 is vaginal ring 50 which is partially loaded into barrel 10.

The embodiments illustrated and discussed in this specification are intended only to teach those skilled in the art the best way known to the inventors to make and use the invention. Nothing in this specification should be considered as limiting the scope of the present invention. All drawings presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

Method of Using

The vaginal ring applicator can be used with any vaginal ring. In certain embodiments, the vaginal ring applicator described herein can be used with NUVARING, which is claimed in U.S. Pat. No. 5,989,581. In other embodiments, the vaginal ring described herein can be used with a vaginal ring that contains etonogestrel. In other embodiments, the vaginal ring described herein can be used with a vaginal ring that contains etonogestrel and ethinyl estradiol. In other embodiments, the vaginal ring described herein can be used with a vaginal ring that contains etonogestrel and 17 beta estradiol. In other embodiments, the vaginal ring described herein can be used with a vaginal ring that comprises ethylene vinylacetate.

Also described herein is the use of a vaginal ring with the vaginal ring applicator described herein. In certain embodiments, described herein is the use of NUVARING with the vaginal ring applicator described herein. In certain embodiments, described herein is the use of a vaginal ring comprising etonogestrel with the vaginal ring applicator described herein. In certain embodiments, described herein is the use of a vaginal ring comprising etonogestrel and ethinyl estradiol with the vaginal ring applicator described herein. In certain embodiments, described herein is the use of a vaginal ring comprising etonogestrel and 17 beta estradiol with the vaginal ring applicator described herein. In certain embodiments, described herein is the use of vaginal ring comprising ethylene vinylacetate with the vaginal ring applicator described herein.

The vaginal ring applicator and the vaginal ring for which the vaginal ring applicator is to be used with can be co-packaged or packaged separately.

Also described herein is a kit comprising: a vaginal ring applicator comprising: a barrel comprising a polymer and at least one friction reducing agent, wherein the barrel is a flattened cylinder having two slightly curved and opposing sides connected by two arcs, wherein the barrel extends between an insertion end and a plunger end; a plunger extending between distal and proximal ends, wherein the distal end of the plunger engages the plunger end of the barrel and wherein the plunger fits telescopically within the barrel, wherein the outer surface is polished; and a vaginal ring comprising etonogestrel and ethinyl estradiol.

Also described herein is a kit comprising: a vaginal ring applicator comprising: a barrel comprising a polymer and at least one friction reducing agent, wherein the barrel is a flattened cylinder having two slightly curved and opposing sides connected by two arcs, wherein the barrel extends between an insertion end and a plunger end; a plunger extending between distal and proximal ends, wherein the distal end of the plunger engages the plunger end of the barrel and wherein the plunger fits telescopically within the barrel, wherein the outer surface is polished; and a vaginal ring comprising etonogestrel and 17 beta estradiol.

Method of Making

In certain embodiments of the vaginal ring applicator described herein, the polymer and friction reducing agents are made by compounding. As used herein, "compounding" refers to preparing polymer formulations by mixing or/and blending polymers and at least one friction reducing agent or other additive in a molten state. In certain embodiments, the polymer/friction reducing agent blends are automatically dosed with fixed set points usually through feeders/hoppers. In certain embodiments, compounding is usually done by extrusion, wherein the extrudate is granulated and the granulate is further processed. In certain embodiments, compounding refers to the thorough mixing of the polymer, dyes and friction reducing agents by blend extrusion and subsequently granulating the polymer blend.

In certain embodiments, the granulate is subsequently used in an injection molding process, forming the applicator parts. In certain embodiments, the barrel and plunger are produced simultaneously in a family mold. The use of a family mold means that both applicator components (barrel and plunger) are produced out of the same compound, i.e. the mold is filled from the same polymer melt in the injection molding process.

During molding, the melted polymer is pressed under high pressure into a metal mold, filling the cavities in the mold which forms the shapes of the barrel and plunger. The plunger, being a single solid part, is molded in a simple (uni-shape) cavity in a mold.

To achieve the hollow flattened cylinder barrel, a metal core is used in the mold. Between this metal core as part of the mold and the mold periphery, only the volume representing the barrel remains. After the polymer melt is pressed inside the mold and cooled sufficiently, the metal core can retracted and the hollow barrel is shaped.

In certain embodiments, the vaginal ring applicators described herein are manufactured by the method of:

compounding a polymer and at least one friction reducing agent to form a barrel granulate for the barrel;

forming a plunger granulate of only the polymer for the plunger;

injection molding the barrel using the barrel granulate; and injection molding the plunger using the plunger granulate.

In certain embodiments, the vaginal ring applicators described herein are manufactured by the method of:

compounding a polymer and at least one friction reducing agent to form a granulate;

injection molding the barrel using the granulate; and injection molding the plunger using the granulate. In certain embodiments, such injection molding processing can be done using a family mold.

EXAMPLE 1

A granulate was made by compounding polypropylene, polydimethylsiloxane, pyrogenic silica and a dye. The granulate was subsequently used in an injection molding process using a family mold, forming the applicator parts. During molding, the melted polymer was pressed under high pressure into a steel/beryllium copper mold, filling the cavities in the mold which forms the shapes of the barrel and plunger. The plunger, being a single solid part, was molded in a simple (uni-shape) cavity in a mold, 6 plungers per shot.

During molding, the melted polymer is pressed under high pressure into a steel mold, filling the cavities in the mold which forms the shapes of the barrel and plunger. The plunger, being a single solid part, is molded in a simple (uni-shape) cavity in a mold, 6 plunger per shot.

To achieve the hollow flattened cylinder barrel, a beryllium copper core was used in the mold. Between this beryllium copper core as part of the mold and the steel mold periphery, only the volume representing the barrel remained. After the polymer melt was pressed inside the mold and cooled sufficiently, the beryllium copper core was retracted and the hollow barrel was shaped. The barrels were produced at a rate of 6 barrels per shot Structure on the inner surface of the barrel was imposed by the surface of the beryllium copper core of the mold. After cooling the injection molded parts, a robot removed 6 barrels and 6 plungers, positioned the plunger relative to a laser printer and, after printing, barrels and plunger, were combined/assembled by same the robot. Subsequently, the assemble applicators were place on a conveyor that moved the assembled applicators into the flow packers for primary packaging.

What is claimed is:

1. A vaginal ring applicator for insertion of a vaginal ring comprising:
    a barrel having an outer surface and an inner surface, comprising a barrel polymer and at least one friction reducing agent, wherein the at least one friction reducing agent is distributed throughout the barrel polymer and reduces a friction coefficient between the inner surface and the vaginal ring, wherein the barrel is a flattened cylinder having two curved and opposing sides connected by two arcs, wherein the barrel extends between an insertion end and a plunger end; and
    a plunger comprising a polymer and extending between distal and proximal ends, wherein the distal end of the plunger engages the plunger end of the barrel and wherein the plunger fits telescopically within the barrel.

2. The vaginal ring applicator of claim 1, wherein a width of the barrel as measured between the two arcs is between 14-15 mm.

3. The vaginal ring applicator of claim 1, wherein a width of the barrel as measured between the two arcs is about 14.3 mm.

4. The vaginal ring applicator of claim 1, wherein a height of the barrel as measured between the two curved and opposing sides is between 7-8 mm.

5. The vaginal ring applicator of claim 1, wherein a height of the barrel as measured between the two curved and opposing sides is about 7.5 mm.

6. The vaginal ring applicator of claim 1, wherein the proximal end of the plunger further comprises a concave shape.

7. The vaginal ring applicator of claim 1, wherein the barrel polymer is polypropylene.

8. The vaginal ring applicator of claim 1, wherein the at least one friction reducing agent is polydimethylsiloxane.

9. The vaginal ring applicator of claim 1, wherein the at least one friction reducing agent is pyrogenic silica.

10. The vaginal ring applicator of claim 1, wherein the vaginal ring applicator is co-packaged with the vaginal ring.

11. The vaginal ring applicator of claim 1, wherein the vaginal ring applicator is co-packaged with the vaginal ring, and wherein the co-packaged vaginal ring comprises etonogestrel.

12. The vaginal ring applicator of claim 1, wherein the vaginal ring applicator is co-packaged with the vaginal ring, and wherein the co-packaged vaginal ring comprises 17 beta estradiol.

13. The vaginal ring applicator of claim 1, wherein the vaginal ring applicator is co-packaged with the vaginal ring, and wherein the co-packaged vaginal ring comprises ethinyl estradiol.

14. Use of the vaginal ring applicator of claim 1 wherein the vaginal ring comprises etonogestrel.

15. Use of the vaginal ring applicator of claim 1 wherein the vaginal ring comprises etonogestrel and ethinyl estradiol.

16. Use of the vaginal ring applicator of claim 1 wherein the vaginal ring comprises etonogestrel and 17 beta estradiol.

17. Use of the vaginal ring applicator of claim 1 wherein the vaginal ring comprises ethylene vinylacetate copolymer.

18. A kit comprising: a vaginal ring applicator for insertion of a vaginal ring comprising:
    a barrel having an outer surface and an inner surface, comprising a barrel polymer and at least one friction reducing agent, wherein the at least one friction reducing agent is distributed throughout the barrel polymer and reduces a friction coefficient between the inner surface and the vaginal ring, wherein the barrel is a flattened cylinder having two curved and opposing sides connected by two arcs, wherein the barrel extends between an insertion end and a plunger end;
    a plunger extending between distal and proximal ends and having an outer surface, wherein the distal end of the plunger engages the plunger end of the barrel and wherein the plunger fits telescopically within the barrel, wherein the outer surface is polished; and
    the vaginal ring comprising etonogestrel and ethinyl estradiol.

19. A kit comprising: a vaginal ring applicator for insertion of a vaginal ring comprising:
    a barrel having an outer surface and an inner surface, comprising a barrel polymer and at least one friction reducing agent, wherein the at least one friction reducing agent is distributed throughout the barrel polymer and reduces a friction coefficient between the inner surface and the vaginal ring, wherein the barrel is a flattened cylinder having two curved and opposing sides connected by two arcs, wherein the barrel extends between an insertion end and a plunger end;
    a plunger extending between distal and proximal ends and having an outer surface, wherein the distal end of the plunger engages the plunger end of the barrel and wherein the plunger fits telescopically within the barrel, wherein the outer surface is polished; and
    the vaginal ring comprising etonogestrel and 17 beta estradiol.

* * * * *